United States Patent
Boerzel et al.

(10) Patent No.: US 6,818,149 B2
(45) Date of Patent: Nov. 16, 2004

(54) LIGAND AND COMPLEX FOR CATALYTICALLY BLEACHING A SUBSTRATE

(75) Inventors: Heidi Boerzel, Boston, MA (US); Peter Comba, Heidelberg (DE); Ronald Hage, Vlaardingen (NL); Marion Kerscher, Heidelberg (DE); Joachim Lienke, Vlaardingen (NL); Michael Merz, Heidelberg (DE)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 332 days.

(21) Appl. No.: 10/021,884

(22) Filed: Dec. 14, 2001

(65) Prior Publication Data

US 2002/0149000 A1 Oct. 17, 2002

(30) Foreign Application Priority Data

Dec. 15, 2000 (GB) ............................................. 0030673

(51) Int. Cl.$^7$ ................................................. C09K 3/00
(52) U.S. Cl. ............................ 252/186.1; 252/186.25; 252/186.33; 540/450; 540/465; 540/470; 540/473; 546/1; 546/2; 546/26
(58) Field of Search .......................... 252/186, 186.33, 252/186.1, 186.25; 546/1, 2, 26; 540/450, 465, 470, 473

(56) References Cited

U.S. PATENT DOCUMENTS

| | | | |
|---|---|---|---|
| 5,882,355 A | 3/1999 | Koek | |
| 6,022,490 A | 2/2000 | Hermant et al. | 252/186.33 |
| 6,107,528 A * | 8/2000 | Que et al. | 568/832 |
| 6,117,833 A | 9/2000 | Racherla et al. | |
| 6,242,409 B1 | 6/2001 | Appel et al. | |
| 6,245,115 B1 | 6/2001 | Appel et al. | |
| 6,340,661 B1 * | 1/2002 | van Deurzen et al. | 510/302 |
| 6,518,231 B2 * | 2/2003 | Appel et al. | 510/367 |

FOREIGN PATENT DOCUMENTS

| | | |
|---|---|---|
| EP | 070 074 | 1/1983 |
| EP | 328 177 | 8/1989 |
| EP | 346 995 | 12/1989 |
| WO | 94/12619 | 6/1994 |
| WO | 94/12620 | 6/1994 |
| WO | 94/12621 | 6/1994 |
| WO | 97/11217 | 3/1997 |
| WO | 97/31090 | 8/1997 |
| WO | WO 97/48787 | 12/1997 |
| WO | 98/38288 | 9/1998 |
| WO | 98/59028 | 12/1998 |
| WO | 99/02632 | 1/1999 |
| WO | 99/02638 | 1/1999 |
| WO | 99/02639 | 1/1999 |
| WO | 99/02641 | 1/1999 |
| WO | 99/23887 | 5/1999 |
| WO | WO 99/65905 | 12/1999 |
| WO | WO 00/12667 | 3/2000 |
| WO | WO 00/12808 | 3/2000 |
| WO | WO 00/29537 | 5/2000 |
| WO | WO 00/60045 | 10/2000 |

OTHER PUBLICATIONS

PCT International Search Report in a PCT application PCT/EP 01/13314, May 2002.
Arzreimittel Forsch., 15(11), pp. 1327–1330 (1965).
GB Search Report.
Arch. Pharm. (Weinheim, Ger) (2000), 333(7), pp. 226–230.
Chem. Eur. J. (1999), 5(6), pp. 1716–1721.
Chemical Abstracts 64:6629d.
J. Chem. Soc. Dalton Trans, 1998(23) pp. 3997–4001.
P. Comba in Coordination Chemistry Reviews 2000, 200–202, pp. 217–245.

* cited by examiner

Primary Examiner—Cephia D. Toomer
(74) Attorney, Agent, or Firm—Milton L. Honig

(57) ABSTRACT

The present invention provides a bleaching composition comprising a [3.3.1] bicyclo compound carrying at least one tertiary amine group the bleaching composition substantially devoid of a peroxygen source.

20 Claims, No Drawings

LIGAND AND COMPLEX FOR CATALYTICALLY BLEACHING A SUBSTRATE

FIELD OF INVENTION

This invention relates to a class of ligand or complex thereof useful as catalysts for catalytically bleaching substrates in an environment substantially devoid of peroxyl species.

BACKGROUND OF INVENTION

The use of bleaching catalysts for stain removal has been developed over recent years. The recent discovery that some catalysts are capable of bleaching effectively in the absence of an added peroxyl source has recently become the focus of some interest, for example: WO9965905; WO0012667; WO0012808, and WO0029537.

The search for new classes of compounds that are suitable as "air bleaching" catalysts is ongoing.

Various [3.3.1] bicyclo compounds and complexes thereof are discussed in the literature, see for example: Comba P. et al., J. Chem. Soc. Dalton Trans, 1998, (23) 3997–4001; Börzel et al. Chem. Eur. J. 1999, 5, No. 6, 1716 to 1721 and review by P. Comba in Coordination Chemistry Reviews 2000, 200–202, 217 to 245, entitled "Coordination compounds in the Entactic State". These compounds are discussed in terms of their physical properties.

WO0060045 discloses a bleaching system comprising: a) from about 1 ppb, by weight of a transition metal catalyst comprising: i) a transition metal; ii) a ligand having formula (I):

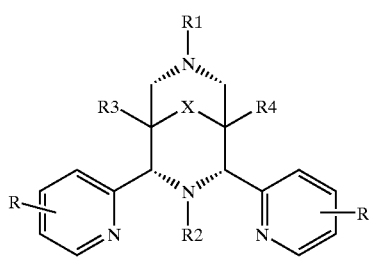

(I)

wherein each R is independently hydrogen, hydroxyl, C1–C4 alkyl, and mixtures thereof; R1 is C1–C4 alkyl, C6–C10 aryl, and mixtures thereof; R2 is C1–C4 alkyl, C6–C10 aryl, and mixtures thereof; R3 and R4 are each independently hydrogen, C1–C8 alkyl, C1–C8 hydroxyalkyl, —(CH$_2$)$_x$CO$_2$R5 wherein R5 is C1–C4 alkyl, x is from 0 to 4, and mixtures thereof; X is carbonyl, —C(R6)2— wherein each R6 is independently hydrogen, hydroxyl, C1–C4 alkyl, and mixtures thereof; b) optionally a source of hydrogen peroxide; and c) the balance carriers and adjunct ingredients. However, the teaching of WO0060045 limits substituents at the nitrogens (3 and 7 positions) of bicyclostructure to homoaromatic carbon groups, namely alkyl and aryl. The general structure of Formula (I) is referred to as a bispidon.

SUMMARY OF INVENTION

The bleaching of a stain by a peroxyl species is aided by the presence of an active transition metal catalyst. A peroxyl species commonly found in laundry bleaching compositions is hydrogen peroxide (H$_2$O$_2$) or a precursor thereof, e.g., sodium percarbonate or sodium perborate. In many instances an activator/precursor, e.g., TAED (tetraacetylethylene diamine), is present which serves together with hydrogen peroxide to form a peracid [RC(O)OOH] to facilitate bleaching.

Recently we have found that oily stains are bleached in the presence of selected transition metal catalysts in the absence of an added peroxyl source. The bleaching of an oily stain in the absence of an added peroxyl source has been attributed to oxygen derived from the air. Whilst it is true that bleaching is effected by oxygen sourced from the air the route in which oxygen plays a part is becoming understood. In this regard, the term "air bleaching" is used.

We have concluded from our research that bleaching of a chromophore in an oily stain is effected by products formed by adventitious oxidation of components in the oily stain. These products, alkyl hydroperoxides, are generated naturally by autoxidation of the oily stain and the alkyl hydroperoxides together with a transition metal catalyst serve to bleach chromophores in the oily stain. Alkyl hydroperoxides (ROOH) are generally less reactive that other peroxy species, for example, peracids (RC(O)OOH), hydrogen peroxide (H202), percarbonates and perborates.

Our earlier filed application PCT/EP01/13314, filed 5, Nov. 2002, which claims priority from GB0030673.8, filed 15, Dec. 2000, discloses the use of various bispidon compounds. Referring to the structure above, PCT/EP01/13314 teaches that there is an advantage to be secured by having at least one of R1 and R2 as group containing a heteroatom capable of coordinating to a transition metal. We have now found that by having at least one of R1 and R2 as a group that is a tertiary amine linked to one or more of the nitrogen atoms of the bicyclo structure by a C2 to C4 alkyl chain further advantages are secured. In addition, we have also found that heterocycles other than pyridyl may be used at the 2 and 4 positions.

Accordingly, in a first aspect, the present invention provides a bleaching composition comprising:

A bleaching composition comprising:
a) a monomer ligand, L, or transition metal catalyst thereof of a ligand having the formula (I):

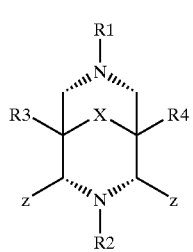

(I)

wherein at least one of R1 and R2 is an optionally substituted tertiary amine of the form —C2–C4-alkyl-NR7R8, in which R7 and R8 are independently selected from the group alkyl, benzyl, the —C2–C4-alkyl- of the —C2–C4-alkyl-NR7R8 may be substituted by 1 to 4 C1–C2-alkyl, or may form part of a C3 to C6 alkyl ring, and in which R7 and R8 may together form a saturated ring containing one or more other heteroatoms, the other of R1 and R2 being independently selected from:
—C2–C4-alkyl-NR7R8 as defined above,
—C1–C24-optionally subsituted-alkyl,
—C6–C10-aryl, —C1–C4-alkyl-C6–C10-aryl,
a heterocycloalkyl: selected from the group consisting of: pyrrolinyl, pyrrolidinyl, morpholinyl, piperidinyl, piperazinyl, hexamethylene imine, 1,4-piperazinyl, tetrahydrothiophenyl, tetrahydrofuranyl, tetrahydropyranyl, and oxazolidinyl, wherein the heterocycloalkyl may be connected to the ligand via any atom in the ring of the selected heterocycloalkyl, a —C1–C6-alkyl-heterocycloalkyl, wherein the heterocycloalkyl of the —C1–C6-heterocycloalkyl is selected from the group consisting of: piperidinyl, piperidine, 1,4-piperazine, tetrahydrothiophene, tetrahydrofuran, pyrrolidine, and tetrahydropyran, wherein the heterocycloalkyl may be connected to the —C1–C6-alkyl via any atom in the ring of the selected heterocycloalkyl, a —C1–C6-alkyl-heteroaryl, wherein the heteroaryl of the —C1–C6-alkylheteroaryl is selected from the group consisting of: pyridinyl, pyrimidinyl, pyrazinyl, triazolyl, pyridazinyl, 1,3,5-triazinyl, quinolinyl, isoquinolinyl, quinoxalinyl, imidazolyl, pyrazolyl, benzimidazolyl, thiazolyl, oxazolidinyl, pyrrolyl, carbazolyl, indolyl, and isoindolyl, wherein the heteroaryl may be connected to the —C1–C6-alkyl via any atom in the ring of the selected heteroaryl and the selected heteroaryl is optionally substituted by —C1–C4-alkyl, —C0–C6-alkyl-phenol, —C0–C6-alkyl-thiophenol, —C2–C4-alkyl-thiol, —C2–C4-alkyl-thioether, —C2–C4-alkyl-alcohol, —C2–C4-alkyl-amine, and a —C2–C4-alkyl-carboxylate;

R3 and R4 are independently selected from hydrogen, C1–C4-alkyl, phenyl, electron withdrawing groups and reduced products and derivatives thereof;

X is selected from: C=O, a ketal derivative of C=O, a thioketal of derivative of C=O, and —[C(R6)$_2$]$_y$— wherein y takes a value 0 or 1; each R6 is independently selected from hydrogen, hydroxyl, O—C1–C24-alkyl, O-benzyl, O—(C=O)—C1–C24-alkyl, C1–C24-alkyl;

z groups are same heteroaromatic groups, selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, and the selected Z is optionally substituted by —C1–C4-alkyl;

b) the balance carriers and adjunct ingredients.

In a second aspect, the present invention provides a bleaching composition comprising, in an aqueous medium, the bicyclo ligand of the general Formula (I) which forms a complex with a transition metal, the complex catalysing bleaching of a substrate, wherein the aqueous medium is substantially devoid of peroxygen bleach or a peroxy-based or -generating bleach system. It is preferred that the medium has a pH value in the range from pH 6 to 12 and most preferably from pH 8 to 11.

The term "substantially devoid of a peroxygen bleach or a peroxy-based or peroxyl-generating bleach system" should be construed within spirit of the invention. It is preferred that the composition has as low a content of peroxyl species present as possible. It is preferred that the bleaching formulation contains less that 1% wt/wt total concentration of peracid or hydrogen peroxide or source thereof, prefereably the bleaching formulation contains less than 0.3% wt/wt total concentration of peracid or hydrogen peroxide or source thereof, most preferably the bleaching composition is devoid of peracid or hydrogen peroxide or source thereof.

An advantage of the class of ligand and complex according to the present invention is that the complex can catalyse bleaching of a substrate via atmospheric oxygen, thus permitting its use in a medium such as an aqueous medium that is substantially devoid of peroxygen bleach or a peroxy-based or -generating bleach system. We have also found that complexes of this class are surprisingly effective in catalysing bleaching of the substrate via atmospheric oxygen after treatment of the substrate.

One skilled in the art will appreciate that not all peroxyl activating catalysts are capable of providing discernable bleaching activity with adventitious hydroperoxides present in a stain. However, the converse is not true. There is no evidence to indicate that any "air bleaching" catalyst will not function as peroxyl activating catalyst. In this regard, all "air bleaching" catalysts disclosed herein may be used as a peroxyl activating catalyst. Catalysts of the present invention may be incorporated into a composition together with a peroxyl species or source thereof. For a discussion of acceptable ranges of a peroxyl species or source thereof and other adjuvants that may be present the reader is directed to U.S. Pat. No. 6,022,490, the contents of which are incorporated by reference.

The present invention extends to a method of bleaching a substrate comprising applying to the substrate, in an aqueous medium, the bleaching composition according to the present invention.

The present invention extends to a commercial package comprising the bleaching composition according to the present invention together with instructions for its use.

The present invention further provides a dry textile having an organic substance as defined above applied or deposited thereon, whereby bleaching via atmospheric oxygen derived alkylhydroperoxides is catalysed on the textile.

Advantageously, by enabling a bleaching effect even after the textile has been treated, the benefits of bleaching can be prolonged on the textile. Furthermore, since a bleaching effect is conferred to the textile after the treatment, the treatment itself, such as a laundry wash cycle, may for example be shortened. Moreover, since a bleaching effect is achieved via atmospheric oxygen after treatment of the textile, hydrogen peroxide or peroxy-based bleach systems can be omitted from the treatment substance.

The organic substance may be contacted to the textile fabric in any suitable manner. For example, it may be applied in dry form, such as in powder form, or in a liquor that is then dried, for example as an aqueous spray-on fabric treatment fluid or a wash liquor for laundry cleaning, or a non-aqueous dry cleaning fluid or spray-on aerosol fluid. Other suitable means of contacting the organic substance to the textile may be used, as further explained below.

Any suitable textile that is susceptible to bleaching or one that one might wish to subject to bleaching may be used. Preferably the textile is a laundry fabric or garment.

In a preferred embodiment, the treated textile is dried, by allowing it to dry under ambient temperature or at elevated temperatures. The elevated temperatures are commonly provided by a heated agitated environment, as for example found in a tumble dryer, which has been found to accelerate and enhance the "air bleaching" effect.

The organic substance can be contacted with the textile fabric in any conventional manner. For example it may be applied in dry form, such as in powder form, or in a liquor that is then dried, for example in an aqueous spray-on fabric treatment fluid or a wash liquor for laundry cleaning, or a non-aqueous dry cleaning fluid or spray-on aerosol fluid.

In a particularly preferred embodiment the method according to the present invention is carried out on a laundry fabric using aqueous treatment liquor. In particular the treatment may be effected in, or as an adjunct to, an essentially conventional wash cycle for cleaning laundry. More preferably, the treatment is carried out in an aqueous detergent wash liquor. The organic substance can be delivered into the wash liquor from a powder, granule, pellet, tablet, block, bar or other such solid form. The solid form can comprise a carrier, which can be particulate, sheet-like or comprise a three-dimensional object. The carrier can be dispersible or soluble in the wash liquor or may remain substantially intact. In other embodiments, the organic substance can be delivered into the wash liquor from a paste, gel or liquid concentrate.

It is particularly advantageous that the organic substance used in the method of the present invention makes use of atmospheric oxygen in its bleaching activity. This avoids the requirement that peroxygen bleaches and/or other relatively large quantities of reactive substances need be used in the treatment process. Consequently, only-a relatively small quantity of bleach active substance need be employed and this allows dosage routes to be exploited that could previously not be used. Thus, while it is preferable to include the organic substance in a composition that is normally used in a washing process, such as a pre-treatment, main-wash, conditioning composition or ironing aid, other means for ensuring that the organic substance is present in the wash liquor may be envisaged.

For example, it is envisaged that the organic substance can be presented in the form of a body from which it is slowly released during the whole or part of the laundry process. Such release can occur over the course of a single wash or over the course of a plurality of washes. In the latter case it is envisaged that the organic substance can be released from a carrier substrate used in association with the wash process, e.g. from a body placed in the dispenser drawer of a washing machine, elsewhere in the delivery system or in the drum of the washing machine. When used in the drum of the washing machine the carrier can be freely moving or fixed relative to the drum. Such fixing can be achieved by mechanical means, for example by barbs that interact with the drum wall, or employ other forces, for example a magnetic force. The modification of a washing machine to provide for means to hold and retain such a carrier is envisaged similar means being known from the analogous art of toilet block manufacture. Freely moving carriers such as shuttles for dosage of surfactant materials and/or other detergent ingredients into the wash can comprise means for the release of the organic substance into the wash.

In the alternative, the organic substance can be presented in the form of a wash additive that preferably is soluble. The additive can take any of the physical forms used for wash additives, including powder, granule, pellet, sheet, tablet, block, bar or other such solid form or take the form of a paste, gel or liquid. Dosage of the additive can be unitary or in a quantity determined by the user. While it is envisaged that such additives can be used in the main washing cycle, the use of them in the conditioning or drying cycle is not hereby excluded.

The present invention is not limited to those circumstances in which a washing machine is employed, but can be applied where washing is performed in some alternative vessel. In these circumstances it is envisaged that the organic substance can be delivered by means of slow release from the bowl, bucket or other vessel which is being employed, or from any implement which is being employed, such as a brush, bat or dolly, or from any suitable applicator.

Suitable pre-treatment means for application of the organic substance to the textile material prior to the main wash include sprays, pens, roller-ball devices, bars, soft solid applicator sticks and impregnated cloths or cloths containing microcapsules. Such means are well known in the analogous art of deodorant application and/or in spot treatment of textiles. Similar means for application are employed in those embodiments where the organic substance is applied after the main washing and/or conditioning steps have been performed, e.g. prior to or after ironing or drying of the cloth. For example, the organic substance may be applied using tapes, sheets or sticking plasters coated or impregnated with the substance, or containing microcapsules of the substance. The organic substance may for example be incorporated into a drier sheet so as to be activated or released during a tumble-drier cycle, or the substance can be provided in an impregnated or microcapsule-containing sheet so as to be delivered to the textile when ironed.

Many transition metal complexes have high extinction coefficients in the visible. In this regard, use over time may result in some colour deposition on a substrate after repeated washing. The addition of a limited amount of a peroxyl source serves to reduce colour deposition in those instances in which it occurs whilst still permitting "air bleaching". Nevertheless, we have found that in certain instances the free ligand may be used in the bleaching composition of the present invention. By using a free ligand, a bleaching formulation may prepared that is consistent with consumer formulation colour expectation. In such a formulation the metal ion may be provided by the composition or by trace metals found in the stain.

DETAILED DESCRIPTION OF THE INVENTION

The ligand as described herein is capable of dynamic inversion. The ability of the ligand to chelate to a TM depends upon the stereochemistry of the substituents. It is preferred that substituents are endo-endo, but it is likely that stereochemical conversion takes place by retro-Mannich conversion. Retro-Mannich may be prevented by changing the groups present such that retro-Mannich reactions are unfavoured. Nevertheless, it is likely that endo-exo and exo-exo ligands as described herein coordinate to transition metal ions in many instances and are capable of functioning as air bleaching catalysts.

Referring to ligands and complexes thereof and bleaching compositions derived therefrom with respect to Formula (I), it is preferred that each z is the same; and R3═R4. Preferred Z groups are pyridine, benzimidazole, thiazole, imidazole. Most preferred z groups are of the form

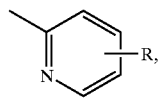

wherein R is independently selected from: hydrogen, F, Cl, Br, hydroxyl, C1–C4-alkyl-, —NH—CO—H, —NH—CO—C1–C4-alkyl, —NH2, —NH—C1–C4-alkyl, and C1–C4-alkyl. Of the R groups it is preferred that R is H or —C1–C4-alkyl.

It is preferred that R3 and R4 are selected from the group consisting of: —CH2OH, —CH2OC(O)C1–C20-alkyl, —C(O)O—C1–C6-alkyl, benzyl ester, —CN, C1–C6-alkyl, benzyl, phenyl, and C1–C4—OR wherein R is selected from the group consisting of H, C1–C24-alkyl or C(O)—C1–C24-alkyl. Most preferred R3 and R4 groups are: —C(O)—O—CH3, —C(O)—O—CH2CH3, benzyl ester, and CH2OH. Notwithstanding the above, R3 and R4 are initially important such that synthesis proceeds to provide bicyclo structure. After the core structure of Formula (I) is formed reduction or other synthetic methods may change R3 and R4. Whilst R3 and R4 may participate in influencing the may be independently selected from electron withdrawing groups and reduced products and derivatives thereof. The R3 and R4 substituents do not have a substantial influence on the catalyst per se except to change the hydrophobisity/solubility of the ligand or transition metal catalyst formed therefrom.

It is preferred that the —C2–C4-alkyl-NR7R8 is selected from the group consisting of: —CH2CH2-NR7R8, —CH2CMe2-NR7R8, -CMe2CH2-NR7R8, —CMeHCH2-NR7R8, —CMeHCMeH-NR7R8, —CH2CMeH-NR7R8, —CH2CH2CH2-NR7R8, —CH2CH2CMe2-NR7R8, —CH2CMe2CH2-NR7R8, —CH2CH2-NEt2, —CH2CR2-N(i-Pr)2,

and

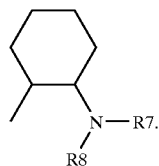

Preferred groups for R7 and R8 are CH3, —C2H5, —C3H7, —C4H9, —C5H11, —C6H13, and —CH2C6H5. It is most preferred that at least one of R7 and R8 is an optionally substituted alkyl chain of at least five carbon atoms.

Other preferred groups for R7 and R8 are —CH3, —CH2CH3, —CH(CH3)2 or where R7 and R8 together with the N form a optionally substituted cyclic structure selected from the group consisting of:

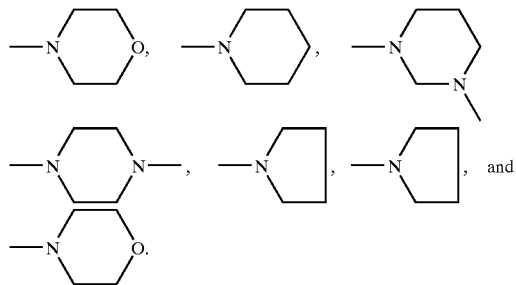

Of the R1 and R2 it is most preferred that R1 is a C2–C4-alkyl-NR7R8 and most preferably both R1 and R2 are independently C2–C4-alkyl-NR7R8. It is preferred that the —C2–C4-alkyl-NR7R8 is a C2-alkyl-NR7R8.

It is preferred that X is selected from: C=O, and —[C(R6)2] wherein each R6 is independently selected from hydrogen, hydroxyl, C1–C24-alkoxy and C1–C24-alkyl. In particular X is preferred in the form C(OH)2, syn-CH(OH) and anti-CH(OH). One skilled in the art will be aware that when X=C(OH)2 a solvent adduct may exist, e.g., when present in methanol the C(OMe)2 adduct will be formed. This adduct will exchange in water such that X=C(OH)2 which again is equilibrium with X=C=O.

Particularly preferred ligands are exemplified below:

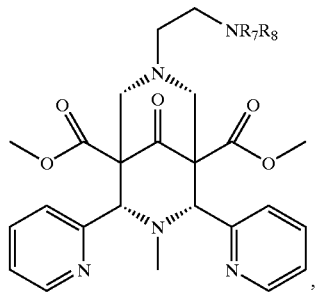

wherein —NR6R7 is selected from the group consisting of —NMe2, NEt2, —N(i-Pr)2,

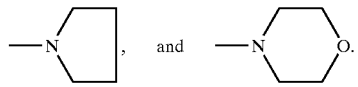

The catalyst may be used as a preformed complex of the ligand and a transition metal. Alternatively, the catalyst may be formed from the free ligand that complexes with a transition metal already present in the water or that complexes with a transition metal present in the substrate. The composition may also be formulated as a composition of the free ligand or a transition metal-substitutable metal-ligand complex, and a source of transition metal, whereby the complex is formed in situ in the medium.

The ligand forms a complex with one or more transition metals, in the latter case for example as a dinuclear complex. Suitable transition metals include for example: manganese in oxidation states II–V, iron II–V, copper I–III, cobalt I–III, titanium II–IV, tungsten IV–VI, vanadium II–V and molybdenum II–VI.

The ligand forms a complex of the general formula (Al):

$$[M_aL_kX_n)Y_m \quad (Al)$$

in which:

M represents a metal selected from Mn(II)–(III)–(IV)–(V), Cu(I)–(II)–(III), Fe(II)–(III)–(IV)–(V), Co(I)–(II)–(III), Tl(II)–(III)–(IV), V(II)–(III)–(IV)–(V), Mo(II)–(III)–(IV)–(V)–(VI) and W(IV)–(V)–(VI), preferably selected from Fe(II)–(III)–(IV)–(V);

L represents a ligand as herein defined, or its protonated or deprotonated analogue;

X represents a coordinating species selected from any mono, bi or tri charged anions and any neutral molecules able to coordinate the metal in a mono, bi or tridentate manner, preferably selected from $O^{2-}$, $RBO_2^{2-}$, $RCOO^-$, $RCONR^-$, $OH^-$, $NO_3^-$, $NO$, $S^{2-}$, $RS^-$, $PO_4^{3-}$, $PO_3OR^{3-}$, $H_2O$, $CO_3^{2-}$, $HCO_3^-$, $ROH$, $N(R)_3$, $ROO^-$, $O_2^{2-}$, $O_2^-$, $RCN$, $Cl^-$, $Br^-$, $OCN^-$, $SCN^-$, $CN^-$, $N_3^-$, $F^-$, $I^-$, $RO^-$, $ClO_4^-$, and $CF_3SO_3^-$, and more preferably selected from $O^{2-}$, $RBO_2^{2-}$, $RCOO^-$, $OH^-$, $NO_3^-$, $S^{2-}$, $RS^-$, $PO_3^{4-}$, $H_2O$, $CO_3^{2-}$, $HCO_3^-$, $ROH$, $N(R)_3$, $Cl^-$, $Br^-$, $OCN^-$, $SCN^-$, $RCN$, $N_3^-$, $F^-$, $I^-$, $RO^-$, $ClO_4^-$, and $CF_3SO_3^-$;

Y represents any non-coordinated counter ion, preferably selected from $ClO_4^-$, $BR_4^-$, $[MX_4]^-$, $[MX_4]^{2-}$, $PF_6^-$, $RCOO^-$, $NO_3^-$, $RO^-$, $N^+(R)_4$, $ROO^-$, $O_2^{2-}$, $O_2^-$, $Cl^-$, $Br^-$, $F^-$, $I^-$, $CF_3SO_3^-$, $S_2O_6^{2-}$, $OCN^-$, $SCN^-$, $H_2O$, $RBO_2^{2-}$, $BF_4^-$, and $BPh_4^-$, and more preferably selected from $ClO_4^-$, $BR_4^-$, $[FeCl_4]^-$, $PF_6^-$, $RCOO^-$, $NO_3^-$, $RO^-$, $N^+(R)_4$, $Cl^-$, $Br^-$, $F^-$, $I^-$, $CF_3SO_3^-$, $S_2O_6^{2-}$, $OCN^-$, $SCN^-$, $H_2O$ and $BF_4^-$;

a represents an integer from 1 to 10, preferably from 1 to 4;

k represents an integer from 1 to 10;

n represents an integer from 1 to 10, preferably from 1 to 4;

m represents zero or an integer from 1 to 20, preferably from 1 to 8; and each R independently represents a group selected from hydrogen, hydroxyl, —R' and —OR', wherein R'=alkyl, alkenyl, cycloalkyl, heterocycloalkyl, aryl, heteroaryl or a carbonyl derivative group, R' being optionally substituted by one or more functional groups E, wherein E independently represents a functional group selected from —F, —Cl, —Br, —I, —OH, —OR', —$NH_2$, —NHR', —$N(R')_2$, —$N(R')_3^+$, —C(O)R', —OC(O)R', —COOH, —$COO^-(Na^+, K^-)$, —COOR', —$C(O)NH_2$, —C(O)NHR', —$C(O)N(R')_2$, heteroaryl, —R', —SR', —SH, —$P(R')_2$, —$P(O)(R')_2$, —$P(O)(OH)_2$, —$P(O)(OR')_2$, —$NO_2$, —$SO_3H$, —$SO_3^-(Na^+, K^+)$, —$S(O)_2R'$, —NHC(O)R', and —N(R')C(O)R', wherein R' represents cycloalkyl, aryl, arylalkyl, or alkyl optionally substituted by —F, —Cl, —Br, —I, —$NH_3^+$, —$SO_3H$, —$SO_3^-(Na^+, K^+)$, —COOH, —$COO^-(Na^+, K^+)$, —$P(O)(OH)_2$, or —$P(O)(O^3(Na^+, K^+))_2$, and preferably each R independently represents hydrogen, optionally substituted alkyl or optionally substituted aryl, more preferably hydrogen or optionally substituted phenyl, naphthyl or $C_{1-4}$-alkyl.

The counter ions Y in formula (Al) balance the charge z on the complex formed by the ligand L, metal M and coordinating species X. Thus, if the charge z is positive, Y may be an anion such as $RCOO^-$, $BPh_4^-$, $ClO_4^-$, $BF_4^-$, $PF_6^-$, $RSO_3^-$, $RSO_4^-$, $SO_4^{2-}$, $NO_3^-$, $F^-$, $Cl^-$, $Br^-$, or $I^-$, with R being hydrogen, optionally substituted alkyl or optionally substituted aryl. If z is negative, Y may be a common cation such as an alkali metal, alkaline earth metal or (alkyl) ammonium cation.

Suitable counter ions Y include those which give rise to the formation of storage-stable solids. Preferred counter ions for the preferred metal complexes are selected from $R^1COO_-$, $ClO_4^-$, $BF_4^-$, $PF_6^-$, $RSO_3^-$ (in particular $CF_3SO_3^-$), $RSO_4^-$, $SO_4^{2-}$, $NO_3^-$, $F^-$, $Cl^-$, $Br^-$, and $I^-$, wherein R represents hydrogen or optionally substituted phenyl, naphthyl or $C_1$–$C_4$ alkyl.

The novel compounds of Formula (I) as provided by the present invention also extend to their various transition metal complexes, the transition metal complexes are as discussed above with reference to (Al).

It will be appreciated that the complex (Al) can be formed by any appropriate means, including in situ formation whereby precursors of the complex are transformed into the active complex of general formula (Al) under conditions of storage or use. Preferably, the complex is formed as a well-defined complex or in a solvent mixture comprising a salt of the metal M and the ligand L or ligand L-generating species. Alternatively, the catalyst may be formed in situ from suitable precursors for the complex, for example in a solution or dispersion containing the precursor materials.

In one such example, the active catalyst may be formed in situ in a mixture comprising a salt of the metal M and the ligand L, or a ligand L-generating species, in a suitable solvent. Thus, for example, if M is iron, an iron salt such as $FeSO_4$ can be mixed in solution with the ligand L, or a ligand L-generating species, to form the active complex. Thus, for example, the composition may formed from a mixture of the ligand L and a metal salt $MX_n$ in which preferably n=1–5, more preferably 1–3. In another such example, the ligand L, or a ligand L-generating species, can be mixed with metal M ions present in the substrate or wash liquor to form the active catalyst in situ. Suitable ligand L-generating species include metal-free compounds or metal coordination complexes that comprise the ligand L and can be substituted by metal M ions to form the active complex according the formula (Al).

The catalysts according to the present invention may be used for laundry cleaning, hard surface cleaning (including cleaning of lavatories, kitchen work surfaces, floors, mechanical ware washing etc.). As is generally known in the art, bleaching compositions are also employed in wastewater treatment, pulp bleaching during the manufacture of paper, leather manufacture, dye transfer inhibition, food processing, starch bleaching, sterilisation, whitening in oral hygiene preparations and/or contact lens disinfection.

In typical washing compositions the level of the organic substance is such that the in-use level is from 1 $\mu$M to 50 mM, with preferred in-use levels for domestic laundry operations falling in the range 10 to 100 $\mu$M. Higher levels may be desired and applied in industrial bleaching processes, such as textile and paper pulp bleaching. These levels reflect the amount of catalyst that may be present in a wash dose of a detergent composition. The bleaching composition comprises at least 1 ppb of the ligand or complex thereof.

In the context of the present invention, bleaching should be understood as relating generally to the decolourisation of stains or of other materials attached to or associated with a substrate. However, it is envisaged that the present invention can be applied where a requirement is the removal and/or neutralisation by an oxidative bleaching reaction of malodours or other undesirable components attached to or otherwise associated with a substrate. Furthermore, in the context of the present invention bleaching is to be understood as being restricted to any bleaching mechanism or process that does not require the presence of light or activation by light.

Synthesis

In addition to the utility of the ligands and complexes of the present invention as catalysts another advantage is that the ligands are generally relatively easy to synthesize in comparison to other ligands. The following is one example of a strategic synthetic approach; it will be evident to one skilled in the art of synthetic organic chemistry that many approaches may be taken to obtain ligands and complexes for use in the present invention. The ease of synthesis of the ligand of Formula (I) is dependent upon the nature of substituents about the structure. The ligands of Formula (I) are most preferably symmetric. Synthesis of these types of molecules are found in articles by U. Holzgrabe et al. in Arch. Pharm. (Weinheim, Ger.) 1992, 325, 657 and A. Samhammer et al. Arch. Pharm. (Weinheim, Ger.) 1984, 322, 557. Below is given a schematic example illustrating the ease of synthesis. The synthesis is shown in a two step synthesis, Scheme 1 and Scheme 2, but in some cases may be conducted asia "one-pot" synthesis depending upon the nature of the substituents. Nevertheless, where substituents at positions 7 and 3 are different a two step synthesis is preferred. The product of reaction as found in Scheme 1 is referred to as dimethyl 2,6-di-(2-pyridyl)-l-methyl-piperid-4-one-3,5-dicarboxylate (NPy2), which can easily tautomerize to the enol. The synthesis is exemplified in R. Haller, K. W. Merz, Pharm. Acta Helv., 1963, 442.

Scheme 1

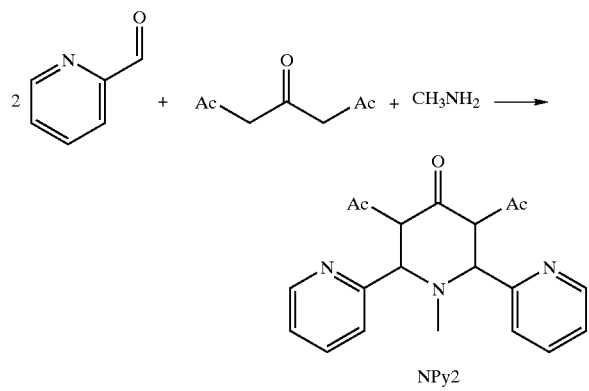

NPy2

Scheme 2

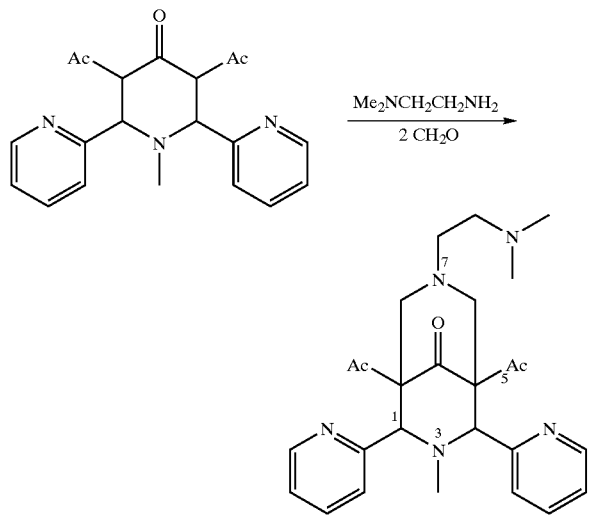

Another intermediate that may be produced according to the general teachings of Scheme 1 wherein MeNH$_2$ is replaced by Me$_2$NCH$_2$CH$_2$NH$_2$ such that a product referred to as dimethyl-2,6-di-(2-pyridyl)-1-(N,N-dimethylamino) ethylene-piperid-4-one-3,5-dicarboxylate is produced, the structure of which is given below.

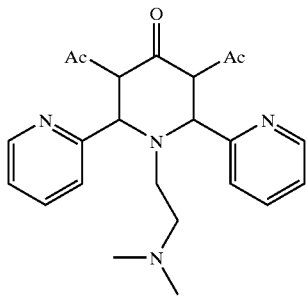

One skilled in the art will appreciate that whilst Ac [—CO(O)Me] is an electron withdrawing group and electron withdrawing groups are generally preferred to facilitate synthesis other groups will also allow the reaction to proceed. Examples of suitable electron withdrawing groups are given above and will be evident to one skilled in the art. The reaction is also driven by precipitation of the product from solution.

In instances, depending upon the nature of the substituents, for example a phenolic group, it will be necessary to protect certain functional groups. The choice of protecting groups during synthesis to prevent undesirable reactions will be evident to one skilled in the art. For a discussion of protecting groups in organic synthesis the reader is directed to T. W. Green and P. G. M. Wuts, Protective Groups In Organic Synthesis 3nd Ed.; J. Wiley and Sons, 1999.

It will be evident that if a diamine is substituted for methylamine in the reaction illustrated in Scheme 2 two structures may be linked together via the 7 positions as found in the structure below.

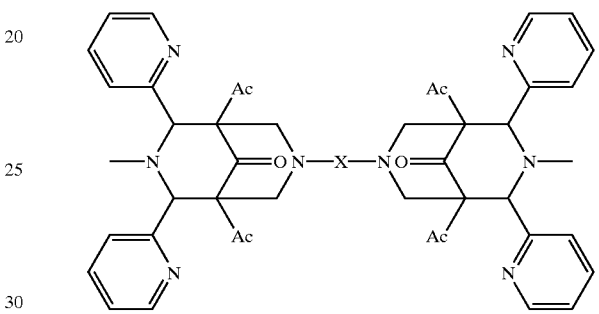

In addition, if a diamine is substituted for methylamine in the reaction illustrated in Scheme 1 a NPy2 structure is formed that is linked at the 3 positions. Obviously, this diner would serve as a precursor to other dimer and polymer type structures. The present invention is confined to "monomer" ligands and not the dimer and polymer units linked by a covalent bond as described above. The term "monomer" as used herein is used to exclude these products in which covalently linked polyligand type structures are formed.

The Detergent Composition

The air bleach catalyst and may be used in a detergent composition specifically suited for stain bleaching purposes, and this constitutes a second aspect of the invention. To that extent, the composition comprises a surfactant and optionally other conventional detergent ingredients. The invention in its second aspect provides an enzymatic detergent composition which comprises from 0.1–50% by weight, based on the total detergent composition, of one or more surfactants. This surfactant system may in turn comprise 0–95% by weight of one or more anionic surfactants and 5 to 100% by weight of one or more nonionic surfactants. The surfactant system may additionally contain amphoteric or zwitterionic detergent compounds, but this in not normally desired owing to their relatively high cost. The enzymatic detergent composition according to the invention will generally be used as a dilution in water of about 0.05 to 2%.

The condition of "the balance carriers and adjunct ingredients" should be taken to be at least 1% wt/wt of a surfactant, preferably at least 5% wt/wt.

In general, the nonionic and anionic surfactants of the surfactant system may be chosen from the surfactants described "Surface Active Agents" Vol. 1, by Schwartz & Perry, Interscience 1949, Vol. 2 by Schwartz, Perry & Berch, Interscience 1958, in the current edition of "McCutcheon's Emulsifiers and Detergents" published by Manufacturing Confectioners Company or in "Tenside-Taschenbuch", H. Stache, 2nd Edn., Carl Hauser Verlag, 1981.

Suitable nonionic detergent compounds which may be used include, in particular, the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are $C_6$–$C_{22}$ alkyl phenol-ethylene oxide condensates, generally 5 to 25 EO, i.e. 5 to 25 units of ethylene oxide per molecule, and the condensation products of aliphatic $C_8$-$C_{18}$ primary or secondary linear or branched alcohols with ethylene oxide, generally 5 to 40 EO.

Suitable anionic detergent compounds which may be used are usually water-soluble alkali metal salts of organic sulphates and sulphonates having alkyl radicals containing from about 8 to about 22 carbon atoms, the term alkyl being used to include the alkyl portion of higher acyl radicals. Examples of suitable synthetic anionic detergent compounds are sodium and potassium alkyl sulphates, especially those obtained by sulphating higher $C_8$–$C_{18}$ alcohols, produced for example from tallow or coconut oil, sodium and potassium alkyl $C_9$-$C_{20}$ benzene sulphonates, particularly sodium linear secondary alkyl $C_{10}$–$C_{15}$ benzene sulphonates; and sodium alkyl glyceryl ether sulphates, especially those ethers of the higher alcohols derived from tallow or coconut oil and synthetic alcohols derived from petroleum. The preferred anionic detergent compounds are sodium $C_{11}$–$C_{15}$ alkyl benzene sulphonates and sodium $C_{12}$–$C_{18}$ alkyl sulphates. Also applicable are surfactants such as those described in EP-A-328 177 (Unilever), which show resistance to salting-out, the alkyl polyglycoside surfactants described in EP-A-070 074, and alkyl monoglycosides.

Preferred surfactant systems are mixtures of anionic with nonionic detergent active materials, in particular the groups and examples of anionic and nonionic surfactants pointed out in EP-A-346 995 (Unilever). Especially preferred is surfactant system that is a mixture of an alkali metal salt of a $C_{16}$–$C_{18}$ primary alcohol sulphate together with a $C_{12}$–$C_{15}$ primary alcohol 3–7 EO ethoxylate.

The nonionic detergent is preferably present in amounts greater than 10%, e.g. 25–90% by weight of the surfactant system. Anionic surfactants can be present for example in amounts in the range from about 5% to about 40% by weight of the surfactant system.

The detergent composition may take any suitable physical form, such as a powder, granular composition, tablets, a paste or an anhydrous gel.

Enzymes

The detergent compositions of the present invention may additionally comprise one or more enzymes, which provide cleaning performance, fabric care and/or sanitation benefits.

Said enzymes include oxidoreductases, transferases, hydrolases, lyases, isomerases and ligases. Suitable members of these enzyme classes are described in Enzyme nomenclature 1992: recommendations of the Nomenclature Committee of the International Union of Biochemistry and Molecular Biology on the nomenclature and classification of enzymes, 1992, ISBN 0-12-227165-3, Academic Press.

Examples of the hydrolases are carboxylic ester hydrolase, thiolester hydrolase, phosphoric monoester hydrolase, and phosphoric diester hydrolase which act on the ester bond; glycosidase which acts on O-glycosyl compounds; glycosylase hydrolysing N-glycosyl compounds; thioether hydrolase which acts on the ether bond; and exopeptidases and endopeptidases which act on the peptide bond. Preferable among them are carboxylic ester hydrolase, glycosidase and exo- and endopeptidases. Specific examples of suitable hydrolases include (1) exopeptidases such as aminopeptidase and carboxypeptidase A and B and endopeptidases such as pepsin, pepsin B, chymosin, trypsin, chymotrypsin, elastase, enteropeptidase, cathepsin B, papain, chymopapain, ficain, thrombin, plasmin, renin, subtilisin, aspergillopepsin, collagenase, clostripain, kallikrein, gastricsin, cathepsin D, bromelain, chymotrypsin C, urokinase, cucumisin, oryzin, proteinase K, thermomycolin, thermitase, lactocepin, thermolysin, bacillolysin. Preferred among them is subtilisin; (2) glycosidases such as α-amylase, β-amylase, glucoamylase, isoamylase, cellulase, endo-1,3(4)-β-glucanase (β-glucanase), xylanase, dextranase, polygalacturonase (pectinase), lysozyme, invertase, hyaluronidase, pullulanase, neopullulanase, chitinase, arabinosidase, exocellobiohydrolase, hexosaminidase, mycodextranase, endo-1,4-β-mannanase (hemicellulase), xyloglucanase, endo-β-galactosidase (keratanase), mannanase and other saccharide gum degrading enzymes as described in WO-A-99/09127. Preferred among them are α-amylase and cellulase; (3) carboxylic ester hydrolase including carboxylesterase, lipase, phospholipase, pectinesterase, cholesterol esterase, chlorophyllase, tannase and wax-ester hydrolase. Preferred among them is lipase.

Examples of transferases and ligases are glutathione S-transferase and acid-thiol ligase as described in WO-A-98/59028 and xyloglycan endotransglycosylase as described in WO-A-98/38288.

Examples of lyases are hyaluronate lyase, pectate lyase, lipex, chondroitinase, pectin lyase, alginase II. Especially preferred is pectolyase, which is a mixture of pectinase and pectin lyase.

Examples of the oxidoreductases are oxidases such as glucose oxidase, methanol oxidase, bilirubin oxidase, catechol oxidase, laccase, peroxidases such as ligninase and those a described in WO-A-97/31090, monooxygenase, dioxygenase such as lipoxygenase and other oxygenases as described in WO-A-99/02632, WO-A-99/02638, WO-A-99/02639 and the cytochrome based enzymatic bleaching systems described in WO-A-99/02641.

The activity of oxidoreductases, in particular the phenol oxidising enzymes in a process for bleaching stains on fabrics and/or dyes in solution and/or antimicrobial treatment can be enhanced by adding certain organic compounds, called enhancers. Examples of enhancers are 2,2'-azo-bis-(3-ethylbenzo-thiazoline-6-sulphonate (ABTS) and Phenothiazine-10-propionate (PTP). More enhancers are described in WO-A-94t12619, WO-A-94/12620, WO-A-94/12621, WO-A-97/11217, WO-A-99/23887. Enhancers are generally added at a level of 0.01% to 5% by weight of detergent composition.

Builders, polymers and other enzymes as optional ingredients may also be present as found in WO0060045.

Suitable detergency builders as optional ingredients may also be present as found in WO0034427.

The invention will now be further illustrated by way of the following non-limiting examples:

EXAMPLES

The ligand N,N-bis(pyridin-2-yl-methyl)-1,1-bis(pyridin-2-yl)-1-aminoethane (MeN4Py) was prepared as described in EP 0 909 809 A2. The synthesis of the iron complex, [(MeN4Py)FeCl]Cl, has been described elsewhere (WO 0116271.

Synthesis

Procedure for Bispidone Synthesis:

A suspension of 7.15 g (16.3 mmol) of piperidone (Npy2) (synthesis exemplified in R. Haller, K. W. Merz, Pharm. Acta Helv., 1963, 442) in 40 ml ethanol is treated with 1.72 g (19.6 mmol) of N,N-dimethylethylendiamine and 3.5 ml of formaldehyde (37% in water)—36.1 mmol) and is refluxed for 30 min. The resulting clear, slight yellow to dark brown reaction solution is evaporated to half of its volume and left at 5° C. for 24 h. The yellow precipitate formed is filtered, washed with little EtOH until the precipitate is white and dried under high vacuum.

If no precipitate is obtained, the reaction mixture is evaporated to dryness, dissolved in as little EtOH as possible and left at 5° C. for 72 h.

Analytical Data:
Melting point: 147° C.
CHN analysis:

| calc. (%) | C 63.02 | H 6.71 | N 14.13 |
|---|---|---|---|
| found (%) | C 62.69 | H 6.76 | N 13.79 |

$FAB^+MS(NBA)$: 496.3 ($MH^+$); $C_{26}H_{33}N_5O_5$ M=495.25 g/mol $IR[cm^{-1}]$: 3039 (w), 2942 (m), 2779 (m), 2760 (m), 2708 (w) 1723 (s), 1587 (m), 1465 (m), 1431(m), 1270 (s), 1162 (m), 971 (m), 751 (m).

$^1$H-NMR (300.133 MHz, $CDCl_3$):δ=1.98 (s, 3H, N—$CH_3$), 2.32 (bs, 6H, N—$(CH_3)_2$), 2.49 (bs, 4H, N—$CH_2$—), 2.61 (d, 2H, $^2J_{HH}$=12.1 Hz, —$CH_2$—), 3.12 (d, 2H, $^2J_{HH}$=9.5 Hz, —$CH_2$—), 3.79 (s, 6H, $OCH_3$), 4.66 (s, 2H, CH—Py), 7.20 (dt, 2H, $^3J_{HH}$=4.8 Hz, $^4J_{HH}$=1.1 Hz, Py-H), 7.73 (dt, 2H, $^3J_{HH}$=7.7 Hz, $^4J_{HH}$=1.8 Hz, Py-H), 8.11 (bd, 2H, $^3J_{HH}$=7.7 Hz, Py-H), 8.47 (dd, 2H, $^3J_{HH}$=8.5 Hz, $^4J_{HH}$=1.1 Hz, Py-H).

$^{13}$C-NMR (75.47 MHz, $CDCl_3$): δ=43.1 (1C, N-$CH_3$), 45.5 (2C, N—$(CH_3)_2$), 52.4 (2C, $OCH_3$), 56.5 (2C, N—$CH_2$), 58.9 (2C, $NCH_2$), 6.42 (2C, $C_{q,Alkyl}$), 73.8 (2C, NCH), 122.9, 136.3, 149.2 (8C, Ar—C), 158.6 (2C, Ar—$C_q$), 168.6 (2C, ester), 207.2 (1C, C=O).

Preparation of Complex 1

2 mmol of metal salt (FeCl2) dissolved in 1 ml methanol is added to 2 mmol of ligand dissolved in 1 ml acetotrile.

After 24 h stirring at RT the solution is concentrated to 0.5 ml total volumne and treated with 5 mL of ethylacetate. The solution is sonicated in an ultrasonic bath. The resulting solid is filtered in dried in high vacuum.

FeCl(N2Py2EtNMe2)]Cl $C_{26}H_{35}Cl_2FeN_5O_6 \cdot H_2O$ M=640.34 g/mol

Analytical Data:
CHN Analysis

| calc. (%) | C 48.77 | H 5.51 | N 10.94 |
|---|---|---|---|
| found (%) | C 49.15 | H 5.79 | N 10.61 |

$FAB^+MS(NR)$: 604.2 [FeCl(N2Py2EtNMe2.$H_2$O)]$H^+$.

Magnetic moment: $\mu$=5.3 B.M

Redox potential: $E_{1/2}$: 847 mV in acetonitrile

IR $[cm^{-1}]$: 3136 (m, OH), 3094 (m), 2976 (m), 1716 (s), 1600 (m), 1472 (m), 1426 (m), 1274 (s), 784 (m), 648 (w).

UV-Vis (MeOH): 402 nm ($\epsilon$=1651 $cm^2$ $mol^{-1}$), 313 nm ($\epsilon$=925 $cm^2$ $mol^{-1}$), 250 nm ($\epsilon$=5123 $cm^2$ $mol^{-1}$), 219 nm (E=4354 $cm^2$ $mol^{-1}$).

Bleaching Experiments (Air Mode)

In an aqueous solution containing 10 mM carbonate buffer (pH 10) with 0.6 g/l NaLAS (linear alkylbenzene sulphonate tomato-soya oil or curry-soya oil stained cloths were added and kept in contact with the solution whilst agitating for 30 minutes at 30° C. Comparative experiments were performed using 10 $\mu$M of the metal complex referred to in the table below.

After the wash, the cloths were rinsed with water and subsequently dried at 30° C. and the change in colour was measured immediately after drying with a Linotype-Hell scanner (ex Linotype) (t=0 in the table). The tomato stains were left for 24 h in the dark and measured again (t=1 in the table). The change in colour (including bleaching) is expressed as the ΔE value versus white; a lower ΔE value means a cleaner cloth. The measured colour difference (ΔE) between the washed cloth and the unwashed cloth is defined as follows:

$$\Delta E = [(\Delta L)^2 + (\Delta a)^2 + (\Delta b)^2]^{1/2}$$

wherein ΔL is a measure for the difference in darkness between the washed and unwashed test cloth; Δa and Δb are measures for the difference in redness and yellowness respectively between both cloths. With regard to this colour measurement technique, reference is made to Commission International de l'Eclairage (CIE); Recommendation on Uniform Colour Spaces, colour difference equations, psychometric colour terms, supplement no 2 to CIE Publication,: no 15, Colormetry, Bureau Central de la CIE, Paris 1978. The results are shown below in the tables.

| Tomato oil (TOL)/pH10 with 0.6 g/l NaLAS | | |
|---|---|---|
| | (t = 0) | (t = 1) |
| Blank | 20 | 20 |
| FeMeN4pyCl2 | 10 | 5 |
| Complex 1 | 11 | 6 |

| Curry oil (COL)/ph10 with 0.6 g/l NaLAS | |
|---|---|
| | (t = 0) |
| Blank | 54 |
| FeMeN4pyCl2 | 46 |
| Complex 1 | 41 |

The experiments presented in the tables above show that the bispidon ligand carrying a tert-amine moiety provides an advantage.

What is claimed is:

1. A bleaching composition comprising:

a) a monomer ligand or transition metal catalyst thereof of a ligand having the formula (I):

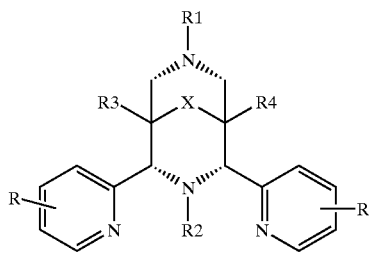

(I)

wherein each R is independently selected from: hydrogen, F, Cl, Br, hydroxyl, C1–C4-alkylO—, —NH—CO—H, —NH—CO—C1–C4-alkyl, —NH2, —NH—C1–C4-alkyl, and C1–C4-alkyl; R1 and R2 are independently selected from:

C1–C4-alkyl,

C6–C10-aryl, and, a group containing a heteroatom capable of coordinating to a transition metal, wherein at least one of R1 and R2 is the group containing the heteroatom;

R3 and R4 are independently selected from hydrogen, C1–C8 alkyl, C1–C8-alkyl-O—C1–C8-alkyl, C1–C8-alkyl-O—C6–C10-aryl, C6–C10-aryl, C1–C8-hydroxyalkyl, and —(CH2)$_n$C(O)OR5 wherein R5 is independently selected from: hydrogen, C1–C6-alkyl, n is from 0 to 4, and mixtures thereof; and, X is selected from C═O, —[C(R6)$_2$]$_y$— wherein Y is from 0 to 3 and each R6 is independently selected from hydrogen, hydroxyl, C1–C4-alkoxy and C1–C4-alkyl; and, b) the balance carriers and adjunct ingredients.

2. A bleaching composition according to claim 1, wherein R1 and R2 are both selected from a group containing a heteroatom capable of coordinating to a transition metal.

3. A bleaching composition according to claim 1, wherein the group containing the heteroatom is:

a heterocycloalkyl: selected from the group consisting of: pyrrolidinyl; pyrrolidinyl; morpholinyl; piperidinyl; piperazinyl; hexamethylene imine; 1,4-piperazinyl; tetrahydrothiophenyl; tetrahydrofuranyl; tetrahydropyranyl; and oxazolidinyl, wherein the heterocycloalkyl may be connected to the ligand via any atom in the ring of the selected heterocycloalkyl, a —C1–C6-alkyl-heterocycloalkyl, wherein the heterocycloalkyl of the —C1–C6-heterocycloalkyl is selected from the group consisting of: piperidinyl; piperidine; 1,4-piperazine, tetrahydrothiophene; tetrahydrofuran; pyrrolidine; and tetrahydropyran, wherein the heterocycloalkyl may be connected to the —C1–C6-alkyl via any atom in the ring of the selected heterocycloalkyl, a —C1–C6-alkyl-heteroaryl, wherein the heteroaryl of the —C1–C6-alkylheteroaryl is selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the —C1–C6-alkyl via any atom in the ring of the selected heteroaryl and the selected heteroaryl is optionally substituted by —C1–C4-alkyl, a —C0–C6-alkyl-phenol or thiophenol, a —C2–C4-alkyl-thiol, thioether or alcohol, a —C2–C4-alkyl-amine, and a —C2–C4-alkyl-carboxylate.

4. A bleaching composition according to claim 1, wherein: each R is the same; and R3═R4.

5. A bleaching composition according to claim 1, wherein R3 and R4 are the same and are —(CH2)$_n$C(O)O—C1–C4-alkyl.

6. A bleaching composition according to claim 1, wherein R3 and R4 are selected from the group consisting of —CH2OH, —C(O)O—C1–C6-alkyl, and phenyl.

7. A bleaching composition according to claim 1, wherein at least one R1 and R2 is a 3-C0–C6-alkyl-pyridin-2-yl-C0–C6-alkyl.

8. A bleaching composition according to claim 1, wherein Y═1.

9. A bleaching composition according to claim 1, wherein R3 and R4 are —C(O)O—C1–C6-alkyl.

10. A bleaching composition according to claim 1, wherein at least one of R1 and R2 is selected from the group consisting of: 3-ethyl-pyridin-2-ylmethyl, pyridin-2-ylmethyl, 3-methyl-pyridin-2-ylmethyl, and 6-amide-pyridin-2-ylmethyl.

11. A bleaching composition according to claim 10, wherein at least one of R1 and R2 is pyridin-2-ylmethyl.

12. A bleaching composition according to claim 1, wherein both R1 and R2 are pyridin-2-ylmethyl and R is H.

13. A bleaching composition according to claim 1, wherein X is C═O.

14. A bleaching composition according to claim 1, wherein the bleaching composition comprises the free ligand.

15. A bleaching composition according to claim 1 wherein the transition metal catalyst is of the general formula (A1):

$$[M_aL_kX_n]Y_m \quad (A1)$$

in which:

M represents a metal selected from Mn(II)–(III)–(IV)–(V), Cu(I)–(II)–(III), Fe(II)–(III)–(IV)–(V), Co(I)–(II)–(III), Ti(II)–(III)–(IV), V(II)–(III)–(IV)–(V), Mo(II)–(III)–(IV)–(V)–(VI) and W(IV)–(V)–(VI);

X represents a coordinating species selected from any mono, bi or tri charged anions and any neutral molecules able to coordinate the metal in a mono, bi or tridentate manner;

Y represents any non-coordinated counter ion;

a represents an integer from 1 to 10;

k represents an integer from 1 to 10;

n represents an integer from 1 to 10;

m represents zero or an integer from 1 to 20; and

L represents a ligand as defined in claim 1, or its protonated or deprotonated analogue.

16. A bleaching composition according to claim 15, wherein M represents a metal selected from Fe(II)–(III)–(IV)–(V).

17. A bleaching composition according to claim 16, wherein M represents a metal selected from Fe(II) and Fe(III).

18. A bleaching composition according to claim 1 wherein the formula (I) ligand excludes the following compounds:

dimethyl 2,4-di-(2-pyridyl)-3,7-bis-(pyridin-2-ylmethyl)-3,7-diaza-bicyclo[3.3.1]nonan-9-one-1,5-dicarboxylate;

1,5-bis-(hydroxymethylene)-2,4-di-(2-pyridyl)-3,7-bis-(pyridin-2-ylmethyl)-3,7-diazabicyclo[3.3.1]nonan-9-ol;

dimethyl 2,4-di-(2-pyridyl)-3,7-bis-(pyridin-2-ylethyl)-3,7-diaza-bicyclo[3.3.1]nonan-9-one-1,5-dicarboxylate;

dimethyl 2,4-di-(2-pyridyl)-3-(5-carboxypentyl)-7-methyl-3,7-diaza-bicyclo[3.3.1]nonan-9-one-1,5-dicarboxylate; dimethyl 2,4-di-(2-pyridyl)-3-(2-methoxyethyl)-7-methyl-3,7-diaza-bicyclo[3.3.1]nonan-9-one-1,5-dicarboxylate; diethyl-2,4-dipyridyl-7-picolyl-3,7-diaza-bicyclo-[3.3.1]-nonan-9-one-1,5-dicarboxylate; diethyl-2,4-dipyridyl-7-benzyl-3-hydroxyethyl-3,7-diaza-bicyclo-[3.3.1]-nonan-9-one-1,5-dicarboxylate; and, dimethyl-2,4-dipyridyl-7-benzyl-3-hydroxyethyl-3,7-diaza-bicyclo[3.3.1]-nonan-9-one-1,5-dicarboxylate.

19. A bleaching composition according to claim 18, wherein at least one of R1 or R2 is pyridin-2-ylmethyl and the other is selected from —CH3, —C2H5, —C3H7, and —C4H9.

20. A perchlorate salt of dimethyl 2,4-di-(2-pyridyl)-3,7-di-(pyridin-2-ylmethyl)-3,7-diaza-bicyclo[3.3.1]nonan-9-one-1,5-dicarboxylate (N2Py4).

* * * * *